US012679819B2

(12) United States Patent
Ha et al.

(10) Patent No.: US 12,679,819 B2
(45) Date of Patent: Jul. 14, 2026

(54) METHOD OF PREPARING ORGANOSULFUR COMPOUND

(71) Applicant: SOULBRAIN CO., LTD., Gyeonggi-do (KR)

(72) Inventors: Jong Jin Ha, Gyeonggi-do (KR); Ah Rang Lee, Gyeonggi-do (KR); Seok Jong Lee, Gyeonggi-do (KR); Hee Geun Park, Gyeonggi-do (KR); Kwang Ju Jung, Gyeonggi-do (KR); Jeong Geun Park, Gyeonggi-do (KR)

(73) Assignee: SOULBRAIN CO., LTD., Gyeonggi-do (KR)

( * ) Notice: Subject to any disclaimer, the term of this patent is extended or adjusted under 35 U.S.C. 154(b) by 597 days.

(21) Appl. No.: 18/034,025

(22) PCT Filed: Dec. 18, 2020

(86) PCT No.: PCT/KR2020/018650
§ 371 (c)(1),
(2) Date: Apr. 26, 2023

(87) PCT Pub. No.: WO2022/092429
PCT Pub. Date: May 5, 2022

(65) Prior Publication Data

US 2023/0391743 A1 Dec. 7, 2023

(30) Foreign Application Priority Data

Oct. 27, 2020 (KR) ........................ 10-2020-0140447

(51) Int. Cl.
*C07D 327/10* (2006.01)
*B01J 27/13* (2006.01)

(52) U.S. Cl.
CPC ............ *C07D 327/10* (2013.01); *B01J 27/13* (2013.01)

(58) Field of Classification Search
CPC .................................................... C07D 327/10
See application file for complete search history.

(56) References Cited

FOREIGN PATENT DOCUMENTS

| | | | |
|---|---|---|---|
| CN | 1037510 | A | 11/1989 |
| CN | 102241662 | A | 11/2011 |
| CN | 104744427 | A | 7/2015 |
| CN | 104945286 | A | 9/2015 |
| CN | 105481826 | A | 4/2016 |
| CN | 109485633 | A | 3/2019 |
| CN | 111533728 | A | 8/2020 |
| KR | 10-1991-0003712 | B1 | 6/1991 |
| KR | 10-2080198 | B1 | 4/2020 |

OTHER PUBLICATIONS

Øystein Rist et al., "Synthesis of Hydroxy Sulfonate Surfactants" Molecules 2005, 10, 1169-1178 (Sep. 30, 2005).

*Primary Examiner* — John S Kenyon
(74) *Attorney, Agent, or Firm* — SZDC Law PC

(57) ABSTRACT

The present invention relates to a method of preparing an organosulfur compound, and more particularly, to a method of preparing an organosulfur compound including a step of synthesizing an organosulfur compound by reacting specific compounds with a metal hypohalite under a ruthenium catalyst in a mixed solvent containing water and an organic solvent, wherein the metal hypohalite is introduced in a solid state and a portion thereof reacts in an undissolved state. According to the present invention, the present invention has an effect of providing an organosulfur compound preparation method capable of preparing an organosulfur compound in high yield due to excellent reaction stability, short reaction time, and reduced side reactions.

18 Claims, 1 Drawing Sheet

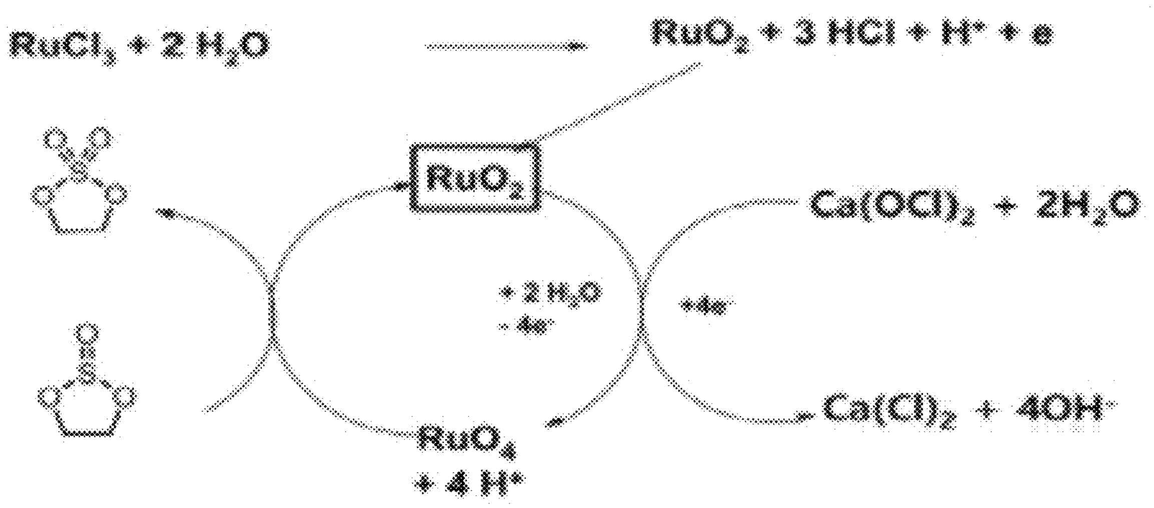
RuCl3 + 2 H2O
RuO2 + 3 HCl + H+ + e
RuO2
Ca(OCl)2 + 2H2O
+ 2 H2O
- 4e-
+4e
Ca(Cl)2 + 4OH-
RuO4
+ 4 H+

METHOD OF PREPARING ORGANOSULFUR COMPOUND

This application is the National Stage Application of PCT/KR2020/018650, filed on Dec. 18, 2020, which claims priority to Korean Patent Application No. KR 10-2020-0140447, filed on Oct. 27, 2020, which is incorporated by reference for all purposes as if fully set forth herein.

TECHNICAL FIELD

The present invention relates to a method of preparing an organosulfur compound, and more particularly, to an organosulfur compound preparation method capable of preparing an organosulfur compound in high yield due to excellent reaction stability, short reaction time, and reduced side reactions.

BACKGROUND ART

Organosulfur compounds such as a sulfoxide-based compound (R—SO—R') and a sulfite-based compound (R—O—SO—O—R') may be used as starting materials to prepare a sulfone-based compound (R—$SO_2$—R') and a sulfate-based compound (R—O—$SO_2$—O—R') through an oxidation-reduction reaction.

The prepared sulfone-based compound (R—$SO_2$—R') and sulfate-based compound (R—O—$SO_2$—O—R') commonly contain the form of —$SO_2$—, and are used in various industrial fields as functional materials such as fuel additives and electrolyte solutions for lithium ion batteries.

Accordingly, a method of efficiently synthesizing a sulfone compound and a sulfate compound in high yield is being actively studied. For example, a technique using a sulfoxide-based compound (R—SO—R') and a sulfite-based compound (R—O—SO—O—R') as starting materials and using sodium hydrogenperiodate ($NaIO_4$), sodium hypochlorite (NaOCl), calcium hypochlorite ($Ca(OCl)_2$), hydrogen peroxide (HOOH), and calcium permanganate ($KMnO_4$) as oxidants is known.

Since these oxidants have high solubility in water, a technique for conveniently storing and using the oxidants in an aqueous solution has been proposed. However, purity and yield may be significantly reduced due to poor reaction stability and vulnerability of a product to water, or reproducibility may be reduced due to a two-phase reaction. In addition, sodium hydrogenperiodate ($NaIO_4$) is not suitable for industrial use due to very high cost thereof.

RELATED ART DOCUMENTS

Patent Documents (Patent Document 1) KR 10-2080198 B1

DISCLOSURE

Technical Problem

Therefore, the present invention has been made in view of the above problems, and it is one object of the present invention to provide a method of preparing an organosulfur compound.

The above and other objects can be accomplished by the present invention described below.

Technical Solution

In accordance with one aspect of the present invention, provided is a method of preparing an organosulfur compound, the method including synthesizing one or more selected from compounds represented by Chemical Formulas 2-1 to 2-3 below by reacting one or more selected from compounds represented by Chemical Formulas 1-1 to 1-3 below with a metal hypohalite under a ruthenium catalyst in a mixed solvent containing water and an organic solvent, wherein the metal hypohalite is introduced in a solid state and a portion thereof reacts in an undissolved state:

[Chemical Formula 1-1]

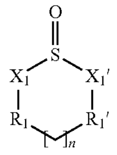

[Chemical Formula 1-2]

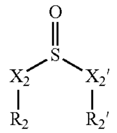

[Chemical Formula 1-3]

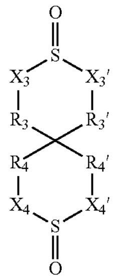

[Chemical Formula 2-1]

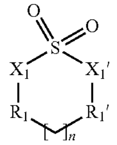

[Chemical Formula 2-2]

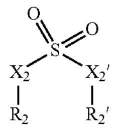

[Chemical Formula 2-3]

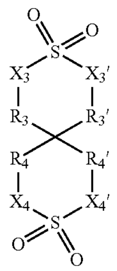

wherein, in Chemical Formulas 1-1, 1-3, 2-1, and 2-3, $X_1$, $X_3$, $X_4$, $X_1'$, $X_3'$, and $X_4'$ are each independently a bond, oxygen, or methylene; n is an integer from 0 to 4; when n is 0, $R_1$, $R_3$, $R_4$, $R_1'$, $R_3'$, and $R_4'$ are each independently hydrogen or a substituted or unsubstituted alkylene having 1 to 10 carbon atoms; and when n is an integer from 1 to 4, $R_1$, $R_3$, $R_4$, $R_1'$, $R_3'$, and $R_4'$ are each independently a bond or a substituted or unsubstituted alkylene having 1 to 10 carbon atoms and include at least one carbon, and in Chemical Formulas 1-2 and 2-2, $X_2$ and $X_2'$ are each independently a bond, oxygen, or methylene; and $R_2$ and $R_2'$ are each independently hydrogen or a substituted or unsubstituted alkyl having 1 to 10 carbon atoms.

The organic solvent may be methylene chloride, dimethyl carbonate, acetonitrile, or a mixture thereof.

Based on 100 parts by weight of the compounds represented by Chemical Formulas 1-1 to 1-3, the water may be added in an amount of 350 to 800 parts by weight.

A weight ratio of the water to the organic solvent is preferably 1:0.8 to 1:4.

The ruthenium catalyst may be ruthenium chloride.

Based on 1 equivalent of the compounds represented by Chemical Formulas 1-1 to 1-3, the ruthenium catalyst may be added in an amount of 0.0001 to 0.0006 equivalent.

The metal hypohalite is preferably calcium hypochlorite.

Based on 1 equivalent of the compounds represented by Chemical Formulas 1-1 to 1-3, the metal hypohalite may be added in an amount of 0.1 to 1.1 equivalent.

The metal hypohalite may be added dropwise at a temperature of 0 to 25° C.

When a preparation reaction scale of the organosulfur compound is 1 kg or more, the metal hypohalite is preferably added dropwise at a temperature of 0 to 5° C.

During the synthesis, dropping temperature may be maintained equal to reaction temperature when the above-described metal hypohalite is added.

During the synthesis, the reaction temperature may be 0 to 25° C.

The mixed solvent may include a weak base.

Based on 1 equivalent of the compounds represented by Chemical Formulas 1-1 to 1-3, the weak base may be added in an amount of 0.1 to 0.5 equivalent.

The reaction is preferably performed at a pH of 7 to 9.

The compounds represented by Chemical Formulas 1-1 to 1-3 may be a compound represented by Chemical Formula 3-1 or 3-2 below, and the compounds represented by Chemical Formulas 2-1 to 2-3 may be a compound represented by Chemical Formula 4-1 or 4-2 below:

[Chemical Formulas 3-1 to 3-2]

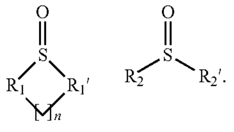

wherein, in Chemical Formula 3-1, $R_1$ and $R_1'$ are each independently hydrogen or a substituted or unsubstituted alkylene having 1 to 10 carbon atoms, and in Chemical Formula 3-2, $R_2$ and $R_2'$ are each independently hydrogen or a substituted or unsubstituted alkyl having 1 to 10 carbon atoms, and n is an integer from 1 to 5.

[Chemical Formulas 4-1 to 4-2]

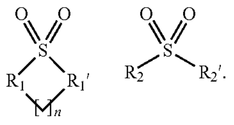

wherein, in Chemical Formula 4-1, $R_1$ and $R_1'$ are each independently hydrogen or a substituted or unsubstituted alkylene having 1 to 10 carbon atoms, and in Chemical Formula 4-2, $R_2$ and $R_2'$ are each independently hydrogen or a substituted or unsubstituted alkyl having 1 to 10 carbon atoms, and n is an integer from 1 to 5.

One or more selected from the compounds represented by Chemical Formulas 1-1 to 1-3 may include one or more selected from compounds represented by Chemical Formulas 3-3 to 3-7 below, and one or more selected from the compounds represented by Chemical Formulas 2-1 to 2-3 may include one or more selected from compounds represented by Chemical Formulas 4-3 to 4-7 below.

[Chemical Formulas 3-3 to 3-7]

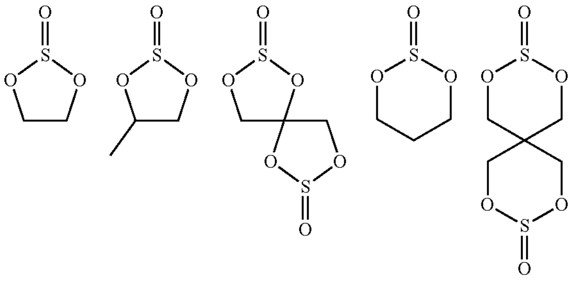

[Chemical Formulas 4-3 to 4-7]

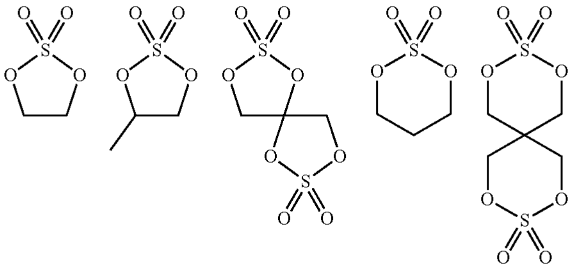

In accordance with another aspect of the present invention, provided is a method of preparing an organosulfur compound, the method including preparing a reactant solution by mixing the mixed solvent and one or more selected from the compounds represented by Chemical Formulas 1-1 to 1-3; adding a ruthenium catalyst to the reactant solution; and adding a metal hypohalite to the reactant solution containing the ruthenium catalyst.

The reaction may be terminated by adding a quenching reagent.

The quenching reagent may be hydrogen peroxide.

In accordance with still another aspect of the present invention, provided is a method of preparing an organosulfur compound, the method including synthesizing one or more selected from the compounds represented by Chemical Formulas 2-1 to 2-3 by reacting one or more selected from the compounds represented by Chemical Formulas 1-1 to 1-3 with a metal hypohalite under a ruthenium catalyst in a mixed solvent containing water and an organic solvent, wherein a weight ratio of the water to the organic solvent is 1:0.8 to 1:1.4.

In accordance with still another aspect of the present invention, provided is a method of preparing an organosulfur compound, the method including synthesizing one or more selected from the compounds represented by Chemical Formulas 2-1 to 2-3 by reacting one or more selected from the compounds represented by Chemical Formulas 1-1 to 1-3 with a metal hypohalite under a ruthenium catalyst in a mixed solvent containing water and an organic solvent, wherein the synthesizing includes preparing a reactant solution by mixing the mixed solvent and the one or more compounds selected from the compounds represented by Chemical Formulas 1-1 to 1-3; adding the ruthenium catalyst to the reactant solution; and adding the metal hypohalite to the reactant solution containing the ruthenium catalyst.

In accordance with still another aspect of the present invention, provided is a method of preparing an organosulfur compound, the method including synthesizing one or more selected from the compounds represented by Chemical Formulas 2-1 to 2-3 by reacting one or more selected from the compounds represented by Chemical Formulas 1-1 to 1-3 with a metal hypohalite under a ruthenium catalyst in a mixed solvent containing water and an organic solvent, wherein, based on 1 equivalent of the compounds represented by Chemical Formulas 1-1 to 1-3, the ruthenium catalyst is added in an amount of 0.0001 to 0.0006 equivalent.

In accordance with still another aspect of the present invention, provided is a method of preparing an organosulfur compound, the method including synthesizing one or more selected from the compounds represented by Chemical Formulas 2-1 to 2-3 by reacting one or more selected from the compounds represented by Chemical Formulas 1-1 to 1-3 with a metal hypohalite under a ruthenium catalyst in a mixed solvent containing water and an organic solvent, wherein a pH of a reaction solution is 7 to 9 during the synthesis.

In accordance with yet another aspect of the present invention, provided is a method of preparing an organosulfur compound, the method including synthesizing one or more selected from the compounds represented by Chemical Formulas 2-1 to 2-3 by reacting one or more selected from the compounds represented by Chemical Formulas 1-1 to 1-3 with a metal hypohalite under a ruthenium catalyst in a mixed solvent containing water and an organic solvent, wherein, based on 1 equivalent of the compounds represented by Chemical Formulas 1-1 to 1-3, the metal hypohalite is added in an amount of 0.1 to 1.1 equivalent, and the metal hypohalite is calcium hypochlorite.

Advantageous Effects

According to the present invention, the present invention has an effect of providing an organosulfur compound preparation method capable of preparing an organosulfur compound in high yield due to excellent reaction stability, short reaction time, and reduced side reactions.

DESCRIPTION OF DRAWINGS

FIG. 1 illustrates a mechanism by which water in a mixed solvent reacts with a ruthenium catalyst to activate an oxidation-reduction reaction, and shows a process of directly converting a compound represented by Chemical Formula 3-3 shown in the lower left corner to a compound represented by Chemical Formula 4-3 shown in the upper left corner using a ruthenium catalyst and a metal hypohalite.

BEST MODE

Hereinafter, a method of preparing an organosulfur compound according to the present invention will be described in detail with reference to the drawings.

The present inventors confirmed that, when synthesizing a predetermined organosulfur compound from starting materials using a ruthenium catalyst and a metal hypohalite, when a mixed solvent containing water and an organic solvent was used as a solvent and the order of introducing the starting materials was specified, the yield of a target substance was increased due to excellent reaction stability, short reaction time, and reduced side reactions. Based on these results, the present inventors conducted further studies to complete the present invention.

As used in the present invention, the term "alkyl" includes straight-chain, branched-chain, or cyclic hydrocarbon radicals, and the term "alkylene" refers to a divalent radical derived from alkyl. For example, the alkylene includes methylene, ethylene, isobutylene, cyclohexylene, cyclopentylethylene, 2-propenylene, 3-butynylene, and the like.

As used in the present invention, in the expression "substituted or unsubstituted", "substitution" means that one or more hydrogen atoms in a hydrocarbon are each independently replaced with the same or different substituents.

In this case, a commonly used substituent may be used, and for example, the substituent is selected from among halo, alkyl, aryl, and arylalkyl.

For example, in a method of preparing an organosulfur compound according to the present invention, a predetermined organosulfur compound is synthesized by reacting starting materials with a metal hypohalite under a ruthenium catalyst in a mixed solvent containing water and an organic solvent. At this time, the metal hypohalite is introduced in a solid state and a portion thereof reacts in an undissolved state. In this case, reaction stability may be excellent, reaction time may be reduced compared to conventional technologies, and output may be increased by reducing side reactions.

In the present disclosure, unless otherwise specified, the starting materials may include one or more selected from compounds represented by Chemical Formulas 1-1 to 1-3 described below.

In the present disclosure, unless otherwise specified, a material prepared from the starting materials may include one or more selected from compounds represented by Chemical Formulas 2-1 to 2-3 described below.

Hereinafter, each of components required to prepare the organosulfur compound of the present invention will be described in detail.

Starting Materials

In the present disclosure, for example, starting materials used for an oxidation-reduction reaction may include one or more selected from compounds represented by Chemical Formulas 1-1 to 1-3 below.

[Chemical Formula 1-1]

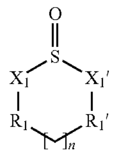

[Chemical Formula 1-2]

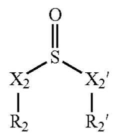

-continued

[Chemical Formula 1-3]

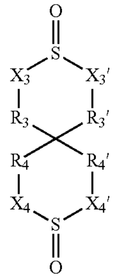

In Chemical Formulas 1-1 and 1-3, $X_1$, $X_3$, $X_4$, $X_1'$, $X_3'$, and $X_4'$ may each independently be a bond, oxygen, or methylene; n may be an integer from 0 to 4; when n is 0, $R_1$, $R_3$, $R_4$, $R_1'$, $R_3'$, and $R_4'$ may each independently be hydrogen or a substituted or unsubstituted alkylene having 1 to 10 carbon atoms; and when n is an integer from 1 to 4, $R_1$, $R_3$, $R_4$, $R_1'$, $R_3'$, and $R_4'$ may each independently be a bond or a substituted or unsubstituted alkylene having 1 to 10 carbon atoms and include at least one carbon.

In addition, in Chemical Formula 1-2, $X_2$ and $X_2'$ may each independently be a bond, oxygen, or methylene, and $R_2$ and $R_2'$ may each independently be hydrogen or a substituted or unsubstituted alkyl having 1 to 10 carbon atoms.

In Chemical Formula 1-1, for example, when $X_1$ and $X_1'$ are each oxygen, n may be 0, and $R_1$ and $R_1'$ may each be a substituted or unsubstituted alkylene having 1 to 10 carbon atoms.

In Chemical Formula 1-1, for example, when $X_1$ and $X_1'$ are each oxygen, n may be an integer from 1 to 4, and $R_1$ and $R_1'$ may each be a substituted or unsubstituted alkylene having 1 to 10 carbon atoms.

In Chemical Formula 1-1, for example, when $X_1$ and $X_1'$ are each methylene, n may be 0, and $R_1$ and $R_1'$ may each be a substituted or unsubstituted alkylene having 1 to 10 carbon atoms.

In Chemical Formula 1-1, for example, when $X_1$ and $X_1'$ are each methylene, n may be an integer from 1 to 4, and $R_1$ and $R_1'$ may each be a substituted or unsubstituted alkylene having 1 to 10 carbon atoms.

In Chemical Formula 1-1, for example, when $X_1$ and $X_1'$ are each a bond, n may be 0, and $R_1$ and $R_1'$ may each be a substituted or unsubstituted alkylene having 1 to 10 carbon atoms.

In Chemical Formula 1-1, for example, when $X_1$ and $X_1'$ are each a bond, n may be an integer from 1 to 4, and $R_1$ and $R_1'$ may each be a substituted or unsubstituted alkylene having 1 to 10 carbon atoms.

In Chemical Formula 1-1, for example, when $X_1$ is methylene and $X_1'$ is oxygen, n may be 0, and $R_1$ and $R_1'$ may each be a substituted or unsubstituted alkylene having 1 to 10 carbon atoms.

In Chemical Formula 1-1, for example, when $X_1$ is methylene and $X_1'$ is oxygen, n may be an integer from 1 to 4, and $R_1$ and $R_1'$ may each independently be a bond or a substituted or unsubstituted alkylene having 1 to 10 carbon atoms.

In addition, in Chemical Formula 1-2, for example, when $X_2$ and $X_2'$ are each oxygen, $R_2$ and $R_2'$ may each be a substituted or unsubstituted alkyl having 1 to 10 carbon atoms.

In Chemical Formula 1-2, for example, when $X_2$ and $X_2'$ are each methylene, $R_2$ and $R_2'$ may each be a substituted or unsubstituted alkyl having 1 to 10 carbon atoms.

In Chemical Formula 1-2, for example, when $X_2$ and $X_2'$ are each a bond, $R_2$ and $R_2'$ may each be a substituted or unsubstituted alkyl having 1 to 10 carbon atoms.

In Chemical Formula 1-2, for example, when $X_2$ is methylene and $X_2'$ is oxygen, $R_2$ and $R_2'$ may each be a substituted or unsubstituted alkyl having 1 to 10 carbon atoms.

In Chemical Formula 1-2, for example, when $X_2$ is methylene and $X_2'$ is oxygen, $R_2$ and $R_2'$ may each independently be a bond or a substituted or unsubstituted alkyl having 1 to 10 carbon atoms.

In addition, in Chemical Formula 1-3, for example, when $X_3$, $X_4$, $X_3'$, and $X_4'$ are each oxygen, $R_3$, $R_4$, $R_3'$, and $R_4'$ may each independently be a bond or a substituted or unsubstituted alkylene having 1 to 10 carbon atoms.

In Chemical Formula 1-3, for example, when $X_3$, $X_4$, $X_3'$, and $X_4'$ are each methylene, $R_3$, $R_4$, $R_3'$, and $R_4'$ may each independently be a substituted or unsubstituted alkylene having 1 to 10 carbon atoms.

In Chemical Formula 1-3, for example, when $X_3$ and $X_4$ are each methylene and $X_3'$ and $X_4'$ are each oxygen, $R_3$, $R_4$, $R_3'$, and $R_4'$ may each independently be a bond or a substituted or unsubstituted alkylene having 1 to 10 carbon atoms.

In addition, one or more selected from the compounds represented by Chemical Formulas 1-1 to 1-3 may include one or more selected from compounds represented by Chemical Formulas 3-1 and 3-2 below.

[Chemical Formulas 3-1 to 3-2]

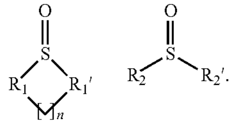

In Chemical Formula 3-1, $R_1$ and $R_1'$ are each independently hydrogen or a substituted or unsubstituted alkylene having 1 to 10 carbon atoms. In Chemical Formula 3-2, $R_2$ and $R_2'$ are each independently hydrogen or a substituted or unsubstituted alkyl having 1 to 10 carbon atoms, and n is an integer from 1 to 5.

As a specific example, one or more selected from the compounds represented by Chemical Formulas 1-1 to 1-3 may include one or more selected from compounds represented by Chemical Formulas 3-3 to 3-7 below.

[Chemical Formulas 3-3 to 3-7]

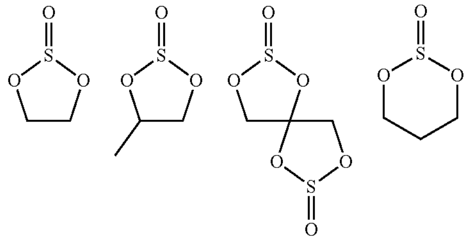

-continued

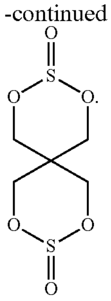

Products

In the present disclosure, for example, products obtained by oxidation-reduction reaction of one or more selected from the compounds represented by Chemical Formulas 1-1 to 1-3 described above may include one or more selected from compounds represented by Chemical Formulas 2-1 to 2-3 below.

[Chemical Formula 2-1]

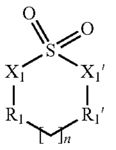

[Chemical Formula 2-2]

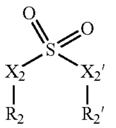

[Chemical Formula 2-3]

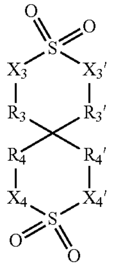

In Chemical Formulas 2-1 and 2-3, $X_1$, $X_3$, $X_4$, $X_1'$, $X_3'$, and $X_4'$ may each independently be a bond, oxygen, or methylene; n may be an integer from 0 to 4; when n is 0, $R_1$, $R_3$, $R_4$, $R_1'$, $R_3'$, and $R_4'$ may each independently be hydrogen or a substituted or unsubstituted alkylene having 1 to 10 carbon atoms; and when n is an integer from 1 to 4, $R_1$, $R_3$, $R_4$, $R_1'$, $R_3'$, and $R_4'$ may each independently be a bond or a substituted or unsubstituted alkylene having 1 to 10 carbon atoms and include at least one carbon.

In addition, in Chemical Formula 2-2, $X_2$ and $X_2'$ may each independently be a bond, oxygen, or methylene, and $R_2$ and $R_2'$ may each independently be hydrogen or a substituted or unsubstituted alkyl having 1 to 10 carbon atoms.

In Chemical Formula 2-1, for example, when $X_1$ and $X_1'$ are each oxygen, n may be 0, and $R_1$ and $R_1'$ may each be a substituted or unsubstituted alkylene having 1 to 10 carbon atoms.

In Chemical Formula 2-1, for example, when $X_1$ and $X_1'$ are each oxygen, n may be an integer from 1 to 4, and $R_1$ and $R_1'$ may each be a substituted or unsubstituted alkylene having 1 to 10 carbon atoms.

In Chemical Formula 2-1, for example, when $X_1$ and $X_1'$ are each methylene, n may be 0, and $R_1$ and $R_1'$ may each be a substituted or unsubstituted alkylene having 1 to 10 carbon atoms.

In Chemical Formula 2-1, for example, when $X_1$ and $X_1'$ are each methylene, n may be an integer from 1 to 4, and $R_1$ and $R_1'$ may each be a substituted or unsubstituted alkylene having 1 to 10 carbon atoms.

In Chemical Formula 2-1, for example, when $X_1$ and $X_1'$ are each a bond, n may be 0, and $R_1$ and $R_1'$ may each be a substituted or unsubstituted alkylene having 1 to 10 carbon atoms.

In Chemical Formula 2-1, for example, when $X_1$ and $X_1'$ are each a bond, n may be an integer from 1 to 4, and $R_1$ and $R_1'$ may each be a substituted or unsubstituted alkylene having 1 to 10 carbon atoms.

In Chemical Formula 2-1, for example, when $X_1$ is methylene and $X_1'$ is oxygen, n may be 0, and $R_1$ and $R_1'$ may each be a substituted or unsubstituted alkylene having 1 to 10 carbon atoms.

In Chemical Formula 2-1, for example, when $X_1$ is methylene and $X_1'$ is oxygen, n may be an integer from 1 to 4, and $R_1$ and $R_1'$ may each independently be a bond or a substituted or unsubstituted alkylene having 1 to 10 carbon atoms.

In addition, in Chemical Formula 2-2, for example, when $X_2$ and $X_2'$ are each oxygen, $R_2$ and $R_2'$ may each be a substituted or unsubstituted alkyl having 1 to 10 carbon atoms.

In Chemical Formula 2-2, for example, when $X_2$ and $X_2'$ are each methylene, $R_2$ and $R_2'$ may each be a substituted or unsubstituted alkyl having 1 to 10 carbon atoms.

In Chemical Formula 2-2, for example, when $X_2$ and $X_2'$ are each a bond, $R_2$ and $R_2'$ may each be a substituted or unsubstituted alkyl having 1 to 10 carbon atoms.

In Chemical Formula 2-2, for example, when $X_2$ is methylene and $X_2'$ is oxygen, $R_2$ and $R_2'$ may each be a substituted or unsubstituted alkyl having 1 to 10 carbon atoms.

In Chemical Formula 2-2, for example, when $X_2$ is methylene and $X_2'$ is oxygen, $R_2$ and $R_2'$ may each independently be a bond or a substituted or unsubstituted alkyl having 1 to 10 carbon atoms.

In addition, in Chemical Formula 2-3, for example, when $X_3$, $X_4$, $X_3'$, and $X_4'$ are each oxygen, $R_3$, $R_4$, $R_3'$, and $R_4'$ may each independently be a bond or a substituted or unsubstituted alkylene having 1 to 10 carbon atoms.

In Chemical Formula 2-3, for example, when $X_3$, $X_4$, $X_3'$, and $X_4'$ are each methylene, $R_3$, $R_4$, $R_3'$, and $R_4'$ may each independently be a substituted or unsubstituted alkylene having 1 to 10 carbon atoms.

In Chemical Formula 2-3, for example, when $X_3$ and $X_4$ are each methylene and $X_3'$ and $X_4'$ are each oxygen, $R_3$, $R_4$, $R_3'$, and $R_4'$ may each independently be a bond or a substituted or unsubstituted alkylene having 1 to 10 carbon atoms.

As a specific example, one or more selected from the compounds represented by Chemical Formulas 2-1 to 2-3 may include one or more selected from compounds represented by Chemical Formulas 4-1 and 4-2 below.

[Chemical Formulas 4-1 to 4-2]

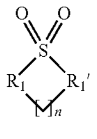

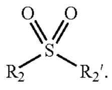

In Chemical Formula 4-1, $R_1$ and $R_1'$ are each independently hydrogen or a substituted or unsubstituted alkylene having 1 to 10 carbon atoms. In Chemical Formula 4-2, $R_2$ and $R_2'$ are each independently hydrogen or a substituted or unsubstituted alkyl having 1 to 10 carbon atoms, and n is an integer from 1 to 5.

In addition, one or more selected from the compounds represented by Chemical Formulas 2-1 to 2-3 may include one or more selected from compounds represented by Chemical Formulas 4-3 to 4-7 below.

[Chemical Formulas 4-3 to 4-7]

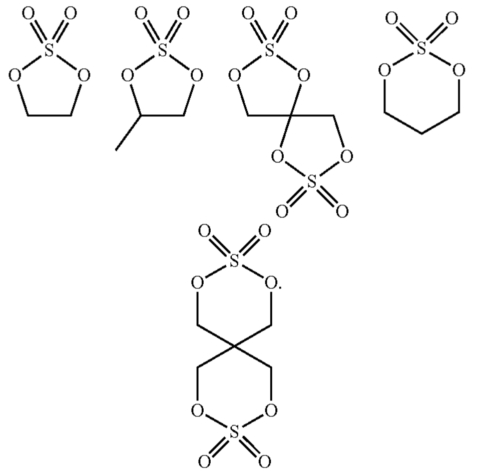

Oxidation-Reduction Reaction

The purpose of the preparation method according to the present invention is to obtain one or more selected from compounds represented by Chemical Formulas 2-1 to 2-3 by an oxidation-reduction reaction using one or more selected from the compounds represented by Chemical Formulas 1-1 to 1-3 described above as starting materials.

The oxidation-reduction reaction is specifically described with reference to the reaction mechanism shown in FIG. 1.

FIG. 1 below is a diagram explaining a reaction mechanism in which water contained in a mixed solvent described later reacts with a ruthenium catalyst to activate an oxidation-reduction reaction.

Referring to FIG. 1, using a ruthenium catalyst and a metal hypohalite, a process of directly converting the compound represented by Chemical Formula 3-3 shown in the lower left corner to the compound represented by Chemical Formula 4-3 shown in the upper left corner is performed.

As shown in FIG. 1 below, in the oxidation-reduction reaction of the present invention, since the order of input of components, types of components, and reaction conditions are specified, reaction stability may be excellent, reaction time may be reduced, and output may be increased due to reduced side reactions.

Hereinafter, a catalyst, solvent, and oxidant necessary for the oxidation-reduction reaction shown in FIG. 1 will be described, and then the specific conditions and time-dependent changes of the oxidation-reduction reaction will be described.

Catalyst for Oxidation-Reduction Reaction

When performing the oxidation-reduction reaction described above, a ruthenium catalyst is added.

In general, the presence of a catalyst increases reaction rate because the reaction may be performed with less activation energy. Catalysts capable of increasing the reaction rate of the oxidation-reduction reaction may be used without limitation. Preferably, a platinum-based catalyst mainly used as a catalyst for oxidation-reduction reaction may be used, more preferably a ruthenium-based catalyst may be used, and most preferably ruthenium chloride may be used.

The ruthenium chloride may be used in anhydrous or hydrated form. For example, based on 1 equivalent of the compounds represented by Chemical Formulas 1-1 to 1-3, the ruthenium chloride may be added in an amount of 0.0001 to 0.0006 equivalent, preferably 0.0005 to 0.0006 equivalent. In this case, by optimizing the aforementioned oxidation-reduction reaction, reaction time may be reduced, and reaction yield may be increased without side reactions.

In particular, according to the preparation process of the present invention, even when the ruthenium chloride is added in a very small amount of 0.0001 to 0.0002 equivalent, the reaction may be performed, thereby reducing production costs.

Oxidant for Oxidation-Reduction Reaction

An oxidant used to perform the above-described oxidation-reduction reaction may be a metal hypohalite.

Examples of suitable metal hypohalites may include hypohalites of alkaline metals or alkaline earth metals, and the hypohalites of alkaline earth metals are preferable considering solubility and reaction efficiency. An alkaline metal also participates in a reaction, but compared to a fact that only 1 mol per 1 mol of a hypohalite oxidant of the alkaline metal participates in the reaction, 2 mol of $OCl^{-1}$ is released per 1 mol, so the oxidation-reduction reaction may be efficiently performed even with a molar amount.

For example, calcium hypochlorite, which is a solid state at room temperature, may be used as the metal hypohalite described above. For the convenience of the process, calcium hypochlorite is dissolved in water to prepare an aqueous calcium hypochlorite solution, and the aqueous calcium hypochlorite solution is used for the reaction. In this case, the amount of water used is significantly increased, and thus production efficiency is greatly reduced. In addition, since some of compounds produced do not ensure stability against water, when the amount of water used increases, yield may decrease. In addition, when the aqueous solution is prepared and added, it is difficult to control reaction rate and heat generation, and as a result, side reactions may occur.

On the other hand, in the present invention, since calcium hypochlorite in a solid state is added and a reaction occurs at the interface between an organic solvent and water, the present invention has an advantage in that reaction rate and heat generation may be easily controlled.

Specifically, according to the mechanism shown in FIG. 1 below, calcium hypochlorite in a solid state is added to a suitable organic solvent to cause an oxidation-reduction reaction between some calcium hypochlorite in an undissolved state and reactants. Therefore, since volume ratio due to water is not increased, production efficiency, purity, and yield may be good, and an exothermic reaction may be controlled. Thus, the calcium hypochlorite according to the present invention may be suitable for mass production processes.

In addition, calcium hypochlorite may be provided in a solid state to provide reaction stability. For example, when calcium hypochlorite with a content of 70% by weight is stored at 4° C. (refrigerated) for 1 month, the content thereof is 69.7% by weight. In addition, when the calcium hypochlorite is stored at 20° C. (room temperature) for 1 month, the content thereof is 69.5% by weight. That is, it can be seen that there is little change in the content of the calcium hypochlorite over time.

For reference, when change over time is confirmed under the same conditions (refrigerated storage or room temperature storage) for sodium hypochlorite, which is usually provided in a liquid state, when sodium hypochlorite with a concentration of 13.9% by weight is stored at 4° C. (refrigerated) for 1 month, the concentration thereof is 13.0% by weight. In addition, when the sodium hypochlorite is stored at 20° C. (room temperature) for 1 month, the concentration thereof is 11.4% by weight. Based on these results, it can be seen that sodium hypochlorite requires refrigeration.

For example, based on 1 equivalent of the compounds represented by Chemical Formulas 1-1 to 1-3, the metal hypohalite may be added in an amount of 0.1 to 1.1 equivalent, preferably 0.1 to 0.7 equivalent, more preferably 0.3 to 0.6 equivalent, most preferably 0.4 to 0.6 equivalent. Within this range, reaction conversion rate and reaction rate may be optimized.

Solvent for Oxidation-Reduction Reaction

Solvents are very important in organic reactions including the aforementioned oxidation-reduction reaction. Even when all other conditions are the same, depending on a solvent, some reactions may not proceed, and some reactions may proceed almost 100%. Accordingly, selection of a solvent is very important in the method for preparing an organosulfur compound according to the present invention.

The solvent should be able to dissolve the compounds represented by Chemical Formulas 1-1 to 1-3 as starting materials. Accordingly, preferably a polar solvent, more preferably a carbonate compound, an alcohol compound, a chloride compound, a nitrile compound, or a mixture thereof, still more preferably methylene chloride, dimethyl carbonate, or a mixture thereof is used as the solvent. In this case, exothermic reaction by water may be controlled, and production efficiency may be improved. In addition, problems occurring when an oxidant and an excess of water as a solvent are used in combination may be minimized.

In addition, it is preferable to use a mixed solvent containing water and the aforementioned organic solvent instead of using the organic solvent alone. At this time, the added water may act as an activator that activates and promotes the overall oxidation-reduction reaction by oxidizing the above-mentioned ruthenium catalyst, which is a catalyst for oxidation-reduction reaction.

Referring again to FIG. 1 below, the ruthenium catalyst reacts with water and is converted into $RuO_2$, 3HCl, and $H^+$. Among the conversion products, $RuO_2$ further reacts with water and is converted into $RuO_4$. Then, $RuO_4$ directly reacts with the above-mentioned oxidant including the metal hypohalite (right pathway), or $RuO_4$ is reduced to $RuO_2$ and $RuO_2$ directly reacts with the compound represented by Chemical Formula 3-3 (left pathway).

These pathways are interlocked and may be specifically described as follows. As shown in the right pathway, ruthenium oxide $RuO_2$ may be oxidized to $RuO_4$ as the hypochlorous acid group of the oxidant is replaced with a halogen group. As shown in the left pathway, the generated $RuO_4$ is reduced to $RuO_2$, and $RuO_2$ directly reacts with the compound represented by Chemical Formula 3-3 so that the compound represented by Chemical Formula 3-3 is directly converted into the compound represented by Chemical Formula 4-3. Thus, reaction time may be reduced, reaction yield may be increased without side reactions, and reaction stability may be increased.

For example, based on 100 parts by weight of the compounds represented by Chemical Formulas 1-1 to 1-3, the water may be added in an amount of 300 to 1,000 parts by weight, preferably 300 to 900 parts by weight, more preferably 300 to 800 parts by weight. Within this range, reaction conversion rate and purity may be optimized.

In addition, the weight ratio of water and the organic solvent constituting the mixed solvent is an important factor affecting the yield and conversion rate of the oxidation-reduction reaction according to the present invention.

For example, in the mixed solvent, the weight ratio of water to the organic solvent (water:organic solvent) may be 1:0.8 or more, preferably 1:0.8 to 1:4, 1:0.9 to 1:3, 1:1 to 1:1.5, or 1:1 to 1:1.3. Within this range, reaction rate and reaction efficiency may be optimized.

For example, by including a weak base, preferably an aqueous weak base solution in the mixed solvent according to the present invention, the effect of buffering decomposition of a hypohalite to hypochloric acid may be provided.

Weak bases that do not affect the reaction may be used as the weak base without limitation. For example, sodium (hydrogen) carbonate, ammonium carbonate, potassium carbonate, ammonium phosphate, sodium phosphate, and the like may be used, and sodium (hydrogen) carbonate is preferably used in consideration of performance and manufacturing cost.

For example, based on 1 equivalent of the compounds represented by Chemical Formulas 1-1 to 1-3, the weak base may be added in an amount of 0.1 to 0.5 equivalent, preferably 0.1 to 0.3 equivalent. Within this range, reaction efficiency may be increased, and pH required for the reaction may be optimized.

Conditions and Time-Dependent Change of Oxidation-Reduction Reaction

For example, the dropping temperature of the metal hypohalite may be 0 to 25° C., 0 to 20° C., 0 to 15° C., or 0 to 5° C. Within this range, reaction stability may be imparted.

For example, the dropping time of the metal hypohalite may be 45 minutes or less, preferably 5 to 40 minutes, more preferably 10 to 40 minutes. In this case, reaction time may be reduced, and yield may be increased.

For example, when the preparation reaction scale of the organosulfur compound is 1 kg or more, the metal hypohalite is preferably added dropwise at a temperature of 0 to 5° C. This case is suitable for pilot and mass production application.

For example, when the preparation reaction scale of the organosulfur compound is 1 kg or more, the metal hypohalite is added dropwise over a period of up to 6 hours, preferably up to 5 hours, more preferably 3 to 4 hours. In this case, when pilot and mass production are applied, reaction time may be reduced, and yield may be increased.

In the present disclosure, the metal hypohalite is introduced in a solid state and a portion thereof reacts in an undissolved state.

For example, during synthesis, when reaction temperature is 0 to 25° C., 0 to 20° C., 0 to 15° C., or 0 to 5° C., a portion of the metal hypohalite introduced in a solid state may react in an undissolved state.

In addition, during the synthesis, considering the reaction efficiency, it is desirable that the reaction temperature maintains the dropping temperature of the metal hypohalite and the suggested reaction temperature range is adjusted.

For example, during the synthesis, the reaction time may be 6 hours or less, preferably 3 hours or less, more preferably 1 hour or less.

In addition, for example, the pH of the synthesis reaction may be 7 to 9, preferably 8 to 8.5, more preferably 8.1 to 8.4. Within this range, reaction efficiency may be optimized.

In the present disclosure, pH may be measured by a measurement method commonly used in the art to which the present invention pertains.

For example, a method of preparing an organosulfur compound according to the present invention includes a step of preparing a reactant solution by mixing the mixed solvent and one or more selected from the compounds represented by Chemical Formulas 1-1 to 1-3; a step of adding a ruthenium catalyst to the reactant solution; and a step of adding a metal hypohalite to the reactant solution containing the ruthenium catalyst, wherein the metal hypohalite is added in a solid state and a portion thereof reacts in an undissolved state. In this case, reaction stability may be excellent, reaction time may be reduced, and yield may be increased due to reduced side reactions.

According to the method of preparing an organosulfur compound according to the present invention, for example, the purity of one or more selected from the compounds represented by Chemical Formulas 2-1 to 2-3 within 1 hour reaction time may be 90% by weight or more, preferably 95% by weight or more, more preferably 99% by weight or more, most preferably 100% by weight.

In addition, according to the method of preparing an organosulfur compound according to the present invention, for example, the yield of the compounds represented by Chemical Formulas 2-1 to 2-3 within 1 hour reaction time may be 79% by weight or more, preferably 80% by weight or more, more preferably 82% by weight or more, still more preferably 85% by weight or more, most preferably 90% by weight or more.

According to the method of preparing an organosulfur compound according to the present invention, after reacting for 1 hour, the reaction was terminated and the purity of a product measured by gas chromatography was 100%.

In addition, according to the preparation method of the present invention, as described above, a product having a purity of 100% by weight or a high purity close thereto is obtained, and the product does not contain insoluble impurities. Accordingly, the reaction may be terminated by introducing a reaction quenching reagent without post-processes such as filter treatment and filtrate purification. At this time, hydrogen peroxide may be used as the reaction quenching reagent.

According to another embodiment of the present invention, the present invention provides a method of preparing an organosulfur compound including a step of synthesizing one or more selected from the compounds represented by Chemical Formulas 2-1 to 2-3 by reacting one or more selected from the compounds represented by Chemical Formulas 1-1 to 1-3 with a metal hypohalite under a ruthenium catalyst in a mixed solvent containing water and an organic solvent, wherein the weight ratio of the water to the organic solvent is 1:0.8 to 1:1.4.

In the present disclosure, the order of addition, reaction conditions, and the content of a metal hypohalite are the same as those described above, so repeated description thereof is omitted.

According to still another embodiment of the present invention, the present invention provides a method of preparing an organosulfur compound including a step of synthesizing one or more selected from the compounds represented by Chemical Formulas 2-1 to 2-3 by reacting one or more selected from the compounds represented by Chemical Formulas 1-1 to 1-3 with a metal hypohalite under a ruthenium catalyst in a mixed solvent containing water and an organic solvent, wherein the step of synthesizing one or more selected from the compounds represented by Chemical Formulas 2-1 to 2-3 includes a step of preparing a reactant solution by mixing the mixed solvent and one or more selected from the compounds represented by Chemical Formulas 1-1 to 1-3; a step of adding a ruthenium catalyst to the reactant solution; and a step of adding a metal hypohalite to the reactant solution containing the ruthenium catalyst.

In the present disclosure, the weight ratio of the mixed solvent, reaction conditions, and the content of the metal hypohalite are the same as those described above, so repeated description thereof is omitted.

According to still another embodiment of the present invention, the present invention provides a method of preparing an organosulfur compound including a step of synthesizing one or more selected from the compounds represented by Chemical Formulas 2-1 to 2-3 by reacting one or more selected from the compounds represented by Chemical Formulas 1-1 to 1-3 with a metal hypohalite under a ruthenium catalyst in a mixed solvent containing water and an organic solvent, wherein, based on 1 equivalent of the compounds represented by Chemical Formulas 1-1 to 1-3, the ruthenium catalyst is added in an amount of 0.0001 to 0.0006 equivalent.

In the present disclosure, the weight ratio of the mixed solvent, the order of addition, reaction conditions, and the content of the metal hypohalite are the same as those described above, so repeated description thereof is omitted.

According to still another embodiment of the present invention, the present invention provides a method of preparing an organosulfur compound including a step of synthesizing one or more selected from the compounds represented by Chemical Formulas 2-1 to 2-3 by reacting one or more selected from the compounds represented by Chemical Formulas 1-1 to 1-3 with a metal hypohalite under a ruthenium catalyst in a mixed solvent containing water and an organic solvent, wherein the pH of the reaction solution is 7 to 9 during the synthesis.

In the present disclosure, the content ratio of the mixed solvent, the order of addition, reaction conditions, and the content of the metal hypohalite are the same as those described above, so repeated description thereof is omitted.

According to yet another embodiment of the present invention, the present invention provides a method of preparing an organosulfur compound including a step of synthesizing one or more selected from the compounds represented by Chemical Formulas 2-1 to 2-3 by reacting one or more selected from the compounds represented by Chemical Formulas 1-1 to 1-3 with a metal hypohalite under a ruthenium catalyst in a mixed solvent containing water and an organic solvent, wherein, based on 1 equivalent of the compounds represented by Chemical Formulas 1-1 to 1-3, the metal hypohalite is added in an amount of 0.1 to 1.1 equivalent, and the metal hypohalite is calcium hypochlorite.

In the present disclosure, the weight ratio of the mixed solvent, the order of addition, and reaction conditions are the same as those described above, so repeated description thereof is omitted.

Hereinafter, the present invention will be described in more detail with reference to the following preferred examples. However, these examples are provided for illustrative purposes only and should not be construed as limiting the scope and spirit of the present invention. In addition, it will be apparent to those skilled in the art that various changes and modifications may be made without departing from the spirit and scope of the present invention, and such changes and modifications are also within the scope of the appended claims.

EXAMPLES

Example 1

A thermometer was installed in a 5 L four-necked reaction vessel, and 100 g of 1,3,2-dioxathiolane 2-oxide (hereinafter referred to as "starting material") as the compound represented by Chemical Formula 3-3, 1,180 g of dimethyl carbonate or methylene chloride, and 728 g of water were added and cooled to 3° C.

Subsequently, based on 1 equivalent of 1,3,2-dioxathiolane 2-oxide, 0.0005 equivalent of ruthenium chloride was added and stirred.

While maintaining the temperature at 3° C., based on 1 equivalent of 1,3,2-dioxathiolane 2-oxide, 0.5 equivalent of calcium hypochlorite in a solid state having a concentration of 70% by weight was added dropwise while maintaining the temperature of the reaction solution at 0 to 5° C. The pH of the reaction solution was maintained at about 8.3 by adding an aqueous sodium hydrogen carbonate solution.

Based on 1 equivalent of 1,3,2-dioxathiolane 2-oxide, 0.2 equivalent of hydrogen peroxide as the reaction quenching reagent was added and stirred for 30 to 60 minutes to separate layers. The separated filtrate was filtered using a celite filter, and the reaction solution was concentrated and recrystallized to obtain a solid product. At this time, the yield was 85% by weight.

Subsequently, vacuum drying was performed at 40° C. to obtain a product, and then gas chromatography was performed. When the purity of 1,3,2-dioxathiolane 2,2-oxide (hereinafter referred to as "product") as the compound represented by Chemical Formula 4-3 was measured, the purity was 100% by weight.

Comparative Example 1

The same procedure as in Example 1 was performed except that reaction was performed for 5 days without using water. As a result, the yield was 20% by weight.

Compared to Example 1, in the case of Comparative Example 1 in which the organic solvent was used for a long time without using the mixed solvent, it was confirmed that the yield decreased to 20% by weight due to a decrease in production due to non-use of water.

Comparative Example 2

The same procedure as in Example 1 was performed except that reaction was performed for 4 days while maintaining the temperature of the reaction solution at 30° C. or higher (specifically 31° C.) without using water. As a result, the yield was less than 5% by weight.

Compared to Example 1, in the case of Comparative Example 2, which the organic solvent was used for a long time at an inappropriate reaction temperature without using the mixed solvent, it was confirmed that the yield decreased to less than 5% by weight due to a sharp decrease in production due to non-use of water.

Examples 2 to 9 and Comparative Examples 3 to 11

The same procedure as in Example 1 was performed except that the type and content of the metal hypohalite added in a solid state, dropping temperature, and dropping time were changed as shown in Table 1 below. The yields of the obtained products were measured, and the results are shown in Table 1 below.

For reference, Examples 1 to 8 are experiments in lab scale units. Example 9 was performed in the same manner as Example 1 except that pilot units were used, 1 kg of 1,3,2-dioxathiolane 2-oxide (hereinafter referred to as "starting material") as the compound represented by Chemical Formula 3-3 was used, and the content ratio provided in Example 1 was used.

TABLE 1

| Classification | Types of metal hypohalites | Metal hypohalite concentration (wt %) | Metal hypohalite content | Dropping temperature of metal hypohalite | Dropping time of metal hypohalite | Yield (wt %) |
|---|---|---|---|---|---|---|
| Example 1 | $Ca(OCl)_2$ | 70% | 0.5 equivalent | 3° C. | 30 minutes | 85% |
| Example 2 | $Ca(OCl)_2$ | 70% | 0.5 equivalent | 5° C | 20 minutes | 83% |
| Example 3 | $Ca(OCl)_2$ | 70% | 0.5 equivalent | 5° C. | 17 minutes | 82% |
| Example 4 | $Ca(OCl)_2$ | 70% | 0.5 equivalent | 5° C. | 30 minutes | 85% |
| Example 5 | $Ca(OCl)_2$ | 70% | 0.5 equivalent | 7° C. | 20 minutes | 82% |
| Example 6 | $Ca(OCl)_2$ | 70% | 0.5 equivalent | 10° C. | 17 minutes | 81% |
| Example 7 | $Ca(OCl)_2$ | 70% | 0.5 equivalent | 15° C. | 15 minutes | 80% |
| Example 8 | $Ca(OCl)_2$ | 70% | 0.5 equivalent | 20° C. | 13 minutes | 78% |
| Example 9 | $Ca(OCl)_2$ | 70% | 0.5 equivalent | 0~5° C. | 240 minutes | 85% |
| Comparative Example 3 | NaOCl | 13.5% | 1 equivalent | 3° C. | 37 minutes | 65% |
| Comparative Example 4 | NaOCl | 13.0% | 1 equivalent | 3° C. | 35 minutes | 60% |
| Comparative Example 5 | NaOCl | 12.6% | 1 equivalent | 3° C. | 34 minutes | 55% |
| Comparative Example 6 | NaOCl | 11.4% | 1 equivalent | 3° C. | 32 minutes | 48% |
| Comparative Example 7 | NaOCl | 13.5% | 1 equivalent | 5° C. | 20 minutes | 44% |
| Comparative Example 8 | NaOCl | 13.5% | 1 equivalent | 5° C. | 22 minutes | 36% |
| Comparative Example 9 | NaOCl | 13.4% | 1 equivalent | 8° C. | 34 minutes | 25% |

TABLE 1-continued

| Classification | Types of metal hypohalites | Metal hypohalite concentration (wt %) | Metal hypohalite content | Dropping temperature of metal hypohalite | Dropping time of metal hypohalite | Yield (wt %) |
|---|---|---|---|---|---|---|
| Comparative Example 10 | NaOCl | 13.4% | 1 equivalent | 10° C. | 32 minutes | 20% |
| Comparative Example 11 | NaOCl | 13.4% | 1 equivalent | 15° C. | 20 minutes | 10% |

The content is given in equivalent based on 1 equivalent of the starting materials.

As shown in Table 1, in the case of Examples 1 to 8 in which 70% by weight of calcium hypochlorite as the metal hypohalite was added at a dropping temperature of 3 to 20° C. for 13 to 30 minutes in lap scale units, it was confirmed that the yields of the products were 78 to 85% by weight. Considering the dropwise addition at a temperature of 0 to 20° C. and the yields of the products, dropwise addition of the metal hypohalite at a temperature of 0 to 5° C. was found to be desirable.

In addition, in the case of Example 9 in which the experiment was performed in pilot units (i.e., using 1 kg of the starting materials) instead of lab scale units of Examples 1 to 8, 70% by weight of calcium hypochlorite was added at a dropping temperature of 0 to 5° C. for 240 minutes, and the yield of the obtained product was 85% by weight.

In addition, in the case of Comparative Examples 3 to 6 in which about 10% by weight of sodium hypochlorite as the metal hypohalite was added at a dropping temperature of 3° C. for 32 to 37 minutes, the yield decreased up to 48% by weight due to a decrease in content according to the dropping time. In the case of Comparative Examples 7 and 8 in which the dropping temperature was increased to 5° C., although the dropping time could be reduced to 20 to 22 minutes, the yield of the product reduced sharply to 36% by weight.

In addition, in the case of Comparative Examples 9 to 11 in which the dropping temperature was increased to 8 to 15° C., although the dropping time was 20 to 34 minutes, the yield of the product reduced dramatically up to 10% by weigh.

Therefore, in the preparation of the organosulfur compound according to the present invention, use of calcium hypochlorite as the metal hypohalite, as well as on a lab scale basis, may increase yield in both pilot and mass production applications. In addition, reaction time may be reduced by adjusting the range of dropping temperatures.

Examples 10 to 16 and Comparative Examples 12 to 16

The same procedure as in Example 1 was performed except that the contents of the organic solvent and water and the dropping temperature and dropping time of calcium hypochlorite were determined according to Table 2 below. The yields of the products were measured, and the results are shown in Table 2 below.

TABLE 2

| Classification | Organic solvent content | Water content | Dropping temperature of calcium hypochlorite | Dropping time of calcium hypochlorite | Yield (wt %) |
|---|---|---|---|---|---|
| Example 10 | 1.2 kg | 1 kg | 5° C. | 30 minutes | 85% |
| Example 11 | 1 kg | 1 kg | 5° C. | 32 minutes | 82% |
| Example 12 | 800 g | 1 kg | 5° C. | 35 minutes | 74% |
| Example 13 | 1.2 kg | 800 g | 5° C. | 32 minutes | 82% |
| Example 14 | 1.2 kg | 500 g | 5° C. | 35 minutes | 79% |
| Example 15 | 1.2 kg | 400 g | 5° C. | 36 minutes | 72% |
| Example 16 | 1.6 kg | 800 g | 5° C. | 90 minutes | 83% |
| Comparative Example 12 | 600 g | 1 kg | 5° C. | 36 minutes | 50% |
| Comparative Example 13 | 400 g | 1 kg | 5° C. | 37 minutes | 30% |
| Comparative Example 14 | 200 g | 1 kg | 5° C. | 40 minutes | 15% |
| Comparative Example 15 | 1.2 kg | 300 g | 5° C. | 37 minutes | 50% |
| Comparative Example 16 | 1.2 kg | 100 g | 5° C. | 40 minutes | 30% |

As shown in Table 2, in the case of Examples 10 to 12 in which 70% by weight of calcium hypochlorite was added at a dropping temperature of 5° C. for 32 to 35 minutes, 1,000 parts by weight of water was used based on 100 parts by weight of the starting materials, and the content ratio of water to the organic solvent (water:organic solvent) was adjusted to 1:0.8 to 1:1.2, it was confirmed that the yields of the products were 74 to 85% by weight. In addition, in the case of Examples 10, 13, 14, and 15 in which 70% by weight of calcium hypochlorite was added at a dropping temperature of 5° C. for 30 to 90 minutes, 400 to 1,000 parts by weight of water was used based on 100 parts by weight of the starting materials, and the content of the organic solvent mixed with the water was 1.2 kg, it was confirmed that the yields of the products were 72 to 85% by weight.

In particular, in the case of Example 16 in which 70% by weight of calcium hypochlorite was added at a dropping temperature of 5° C. for 90 minutes, 400 to 1,000 parts by weight of water was used based on 100 parts by weight of the starting materials, and the content of the organic solvent mixed with the water was increased to 1.6 kg, it was confirmed that the yield of the product was 83% by weight.

In addition, it was confirmed that the purity of the product obtained in Example 13 measured by gas chromatography was 99.98% by weight.

In addition, in the case of Comparative Examples 12 to 16 in which 70% by weight of calcium hypochlorite was added at a dropping temperature of 5° C. for 36 to 40 minutes, the yield decreased as the solvent content decreased or the water content decreased. These results indicate that the reaction does not proceed smoothly when the organic solvent or water is insufficient due to the solubility of materials. Specifically, it was confirmed that the yield of the product sharply decreased to 30% by weight.

Accordingly, in the preparation of the organosulfur compound according to the present invention, when water and the organic solvent are mixed in a ratio of 1:0.8 or more (water:organic solvent), preferably 1:1 or more (water:organic solvent), an effect of increasing reaction yield and decreasing reaction time may be provided.

In addition, in the preparation of the organosulfur compound according to the present invention, when water and the organic solvent are mixed in a ratio of 1:1.2 to 1:3 (water:organic solvent), an effect of increasing reaction yield and decreasing reaction time may be provided.

Comparative Examples 17 and 18

The same procedure as in Example 1 was performed except that the order of addition was changed as shown in Table 3 below. The yields of the obtained products were measured, and the results are shown in Table 3 below.

TABLE 3

| | Order of addition | | | | |
|---|---|---|---|---|---|
| Classification | Organic solvent + water | Starting materials | $RuCl_3$ | $Ca(OCl)_2$ | Yield (wt %) |
| Example 1 | 1 | 2 | 3 | 4 | 85% |
| Comparative Example 17 | 1 (DMC + water) | 4 | 3 | 2 | 10% |
| Comparative Example 18 | 1 (MC + water) | 4 | 3 | 2 | 20 |

(In the table, alphabets 1,2,3, and 4 indicate the order of addition)

As shown in Table 3, in the case of Example 1 in which the order of addition is mixed solvent→starting materials→ruthenium catalyst→metal hypohalite, the yield was 85% by weight. In the case of Comparative Examples 17 and 18 in which the order is changed to mixed solvent→metal hypohalite→ruthenium catalyst→starting materials, the yield was only 10 to 20% by weight.

In particular, in the case of Comparative Example 17 using DMC as the organic solvent, the yield was only 10% by weight, which was lower than the yield (20% by weight) of Comparative Example 18 using MC as the organic solvent.

Comparative Examples 19 and 20

The same procedure as in Example 1 was performed except that the pH of the reaction solution was changed as shown in Table 4 below. The yields of the obtained products were measured, and the results are shown in Table 4 below.

TABLE 4

| Classification | pH of reaction solution | Yield (wt %) |
|---|---|---|
| Example 1 | 8.3 | 85% |
| Comparative Example 19 | 6 | 50% |
| Comparative Example 20 | 5 | 38% |

As shown in Table 4, in the case of Example 1 in which the pH of the reaction solution was 7 to 9, the yield was 85% by weight. On the other hand, in the case of Comparative Examples 19 and 20 in which the pH of the reaction solution was 6 and 5, respectively, the yields were only 50 to 38% by weight. In particular, it was confirmed that the yield of Comparative Example 20 using the reaction solution having a pH of 5 was significantly reduced compared to Example 1 using the reaction solution having a pH of 8.3.

In conclusion, to synthesize a predetermined organosulfur compound, when starting materials are reacted with a specific metal hypohalite in a specific state under a ruthenium catalyst in a mixed solvent containing water and an organic solvent, the input amounts of the water and the organic solvent are adjusted in a specific range, and the components are added in the order of the mixed solvent, the starting materials, the catalyst, and the metal hypohalite, reaction stability may be excellent, reaction time may be reduced, and yield may be increased due to reduced side reactions.

The invention claimed is:

1. A method of preparing an organosulfur compound, comprising synthesizing one or more selected from compounds represented by Chemical Formulas 4-3 to 4-7 below by reacting one or more selected from compounds represented by Chemical Formulas 3-3 to 3-7 below with a metal hypohalite under a ruthenium catalyst in a mixed solvent containing water and an organic solvent, wherein the metal hypohalite is introduced in a solid state and a portion thereof reacts in an undissolved state:

[Chemical Formulas 3-3 to 3-7]

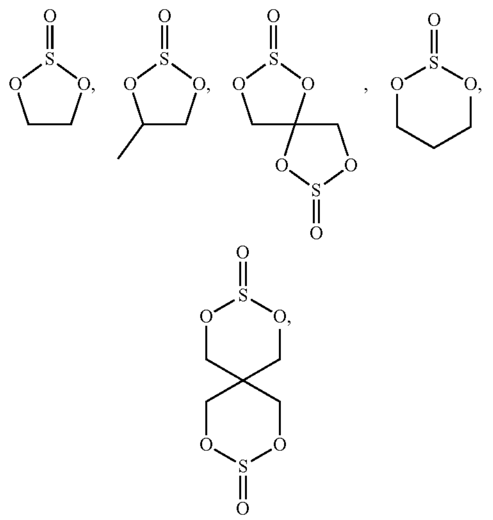

[Chemical Formulas 4-3 to 4-7]

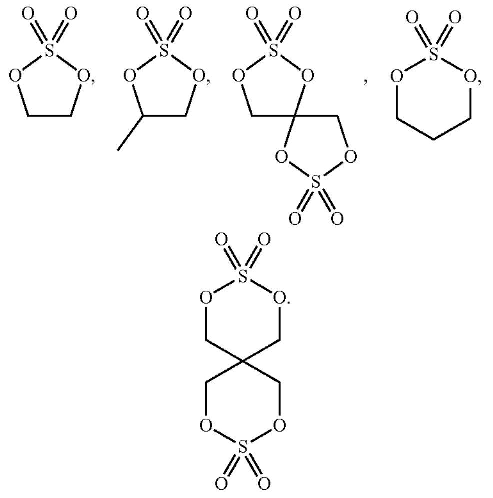

2. The method according to claim 1, wherein the organic solvent is methylene chloride, dimethyl carbonate, or a mixture thereof.

3. The method according to claim 1, wherein, based on 100 parts by weight of the compounds represented by Chemical Formulas 3-3 to 3-7, the water is added in an amount of 300 to 800 parts by weight.

4. The method according to claim 1, wherein a weight ratio of the water to the organic solvent is 1:0.8 to 1:4.

5. The method according to claim 1, wherein the ruthenium catalyst is ruthenium chloride.

6. The method according to claim 1, wherein, based on 1 equivalent of the compounds represented by Chemical Formulas 3-3 to 3-7, the ruthenium catalyst is added in an amount of 0.0001 to 0.0006 equivalent.

7. The method according to claim 1, wherein the metal hypohalite is calcium hypochlorite.

8. The method according to claim 1, wherein, based on 1 equivalent of the compounds represented by Chemical Formulas 3-3 to 3-7, the metal hypohalite is added in an amount of 0.1 to 1 equivalent.

9. The method according to claim 1, wherein the metal hypohalite is added dropwise at a temperature of 0 to 25° C.

10. The method according to claim 1, wherein, when a preparation reaction scale of the organosulfur compound is 1 kg or more, the metal hypohalite is added dropwise at a temperature of 0 to 5° C.

11. The method according to claim 1, wherein, during the synthesis, reaction temperature maintains a dropping temperature of the metal hypohalite.

12. The method according to claim 1, wherein, during the synthesis, the reaction temperature is 0 to 25° C.

13. The method according to claim 1, wherein the mixed solvent comprises a weak base.

14. The method according to claim 13, wherein, based on 1 equivalent of the compounds represented by Chemical Formulas 3-3 to 3-7, the weak base is added in an amount of 0.1 to 0.5 equivalent.

15. The method according to claim 1, wherein the reaction is performed at a pH of 7 to 9.

16. The method according to claim 1, comprising preparing a reactant solution by mixing the mixed solvent and one or more selected from the compounds represented by Chemical Formulas 3-3 to 3-7; adding the ruthenium catalyst to the reactant solution; and adding the metal hypohalite to the reactant solution containing the ruthenium catalyst.

17. The method according to claim 1, wherein the reaction is terminated by adding a quenching reagent.

18. The method according to claim 17, wherein the quenching reagent is hydrogen peroxide.

* * * * *